US011020329B2

(12) United States Patent
Potnis et al.

(10) Patent No.: US 11,020,329 B2
(45) **Date of Patent: *Jun. 1, 2021**

(54) ORAL CARE COMPOSITIONS

(71) Applicant: Colgate-Palmolive Company, New York, NY (US)

(72) Inventors: Shashank Potnis, Thane (IN); Rolando Plata, Las Pinas (PH); Shridhara M Kamath, Mumbai (IN); Nookesh Kotipalli, Andhra Pradesh (IN); Manish Mandhare, Navi Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,642

(22) Filed: Jul. 8, 2019

(65) Prior Publication Data

US 2019/0328634 A1 Oct. 31, 2019

Related U.S. Application Data

(63) Continuation of application No. 15/570,196, filed as application No. PCT/US2016/029313 on Apr. 26, 2016, now Pat. No. 10,363,206.

(30) Foreign Application Priority Data

Apr. 29, 2015 (IN) .......................... 1185/DEL/2015

(51) Int. Cl.

| | |
|---|---|
| ***A61Q 11/00*** | (2006.01) |
| ***A61K 8/19*** | (2006.01) |
| ***A61K 6/00*** | (2020.01) |
| ***A61K 33/10*** | (2006.01) |
| ***A61K 31/198*** | (2006.01) |
| ***A61K 8/21*** | (2006.01) |
| ***A61K 8/24*** | (2006.01) |
| ***A61K 8/44*** | (2006.01) |

(52) U.S. Cl.

CPC .................. *A61K 8/19* (2013.01); *A61K 8/21* (2013.01); *A61K 8/24* (2013.01); *A61K 8/44* (2013.01); *A61Q 11/00* (2013.01); *A61K 2800/42* (2013.01)

(58) Field of Classification Search

CPC ...... A61Q 11/00; A61K 8/21; A61K 2300/00; A61K 2800/52; A61K 2800/592; A61K 2800/20; A61K 2800/42; A61K 9/006; A61K 2800/92; A61K 45/06; A61K 8/19; A61K 33/10

See application file for complete search history.

(56) References Cited

U.S. PATENT DOCUMENTS

| | | | |
|---|---|---|---|
| 4,283,385 | A | 8/1981 | Dhabhar et al. |
| 6,241,974 | B1 | 6/2001 | Adamy |
| 8,652,445 | B2 | 2/2014 | MacDonald et al. |
| 9,308,158 | B2 | 4/2016 | Chandrasekaran et al. |
| 9,682,027 | B2 | 6/2017 | Prencipe et al. |
| 9,717,929 | B2 | 8/2017 | Chopra et al. |
| 2010/0330002 | A1 | 12/2010 | Robinson et al. |
| 2010/0330003 | A1 | 12/2010 | Robinson et al. |
| 2011/0052509 | A1 | 3/2011 | Subramanyam et al. |
| 2013/0224270 | A1 | 8/2013 | Robinson et al. |
| 2013/0230469 | A1 | 9/2013 | Lewus et al. |

FOREIGN PATENT DOCUMENTS

| | | |
|---|---|---|
| CN | 103006457 | 4/2013 |
| WO | 1993/025184 | 12/1993 |
| WO | 2002/030381 | 4/2002 |
| WO | 2007/122146 | 11/2007 |
| WO | 2009/10260 | 8/2009 |
| WO | 2009/100268 | 8/2009 |
| WO | 2013047826 | 4/2013 |
| WO | 2014/185884 | 11/2014 |

OTHER PUBLICATIONS

CN103006457, Ma Meilin, "Calcium carbonate type toothpaste," Apr. 3, 2013, English language machine translation of abstract, Espacenet, date obtained: Dec. 12, 2019, 1 page. <https://worldwide.espacenet.com/patent/search/family/047955928/publication/CN103006457A?q=cn103006457>.

WO2013047826, Lion Corp, "Oral Composition," Apr. 4, 2013, English language machine translation of abstract, Espacenet, date obtained: Dec. 12, 2019, 1 page. <https://worldwide.espacenet.com/patent/search/family/047995849/publication/WO2013047826A1?q=wo2013047826>.

International Search Report and Written Opinion of the International Searching Authority in International Application No. PCT/US2016/029313, dated Aug. 22, 2016.

*Primary Examiner* — Tracy Liu

(57) ABSTRACT

Provided is an oral care composition, e.g., a dentifrice, comprising a calcium abrasive, e.g., calcium carbonate, potassium nitrate ($KNO_3$), and a basic amino acid, in free or salt form, e.g., arginine, in free or salt form, wherein the potassium nitrate is present in an amount of 0.1-1% by weight of the composition and methods of using the same.

18 Claims, No Drawings

ORAL CARE COMPOSITIONS

CROSS-REFERENCE TO RELATED PATENT APPLICATIONS

This application claims the benefit of priority to Indian Patent Application Serial No. 1185/DEL/2015, filed Apr. 29, 2015, the entirety of which is incorporated herein by reference.

BACKGROUND

The different ingredients in calcium carbonate dentifrices should be balanced to ensure that the formula remains stable with no syneresis and, for colored dentifrices, that no color migration or color degradation occurs during the shelf life and when the dentifrice is exposed to high temperatures.

Syneresis in calcium carbonate based dentifrices may be avoided by using high levels of humectants, thickeners like precipitated silica, high quality gums/binders, and quality flavors, and by optimizing surfactant levels, however, such steps may increase the manufacturing cost. Increasing the water content and reducing the amount of humectants, thickeners, gums/binders, and/or flavorants or using lower cost flavorants, may lower the manufacturing cost, however, such steps may also disturb the balance among the ingredients resulting in syneresis and color migration and/or degradation.

In addition, adding new ingredients to calcium carbonate dentifrices may be challenging as the new ingredients may disturb the balance among the ingredients resulting in syneresis and color migration and/or degradation.

Flavor is an important component of dentifrices. Instabilities related to flavor may impact consumer taste and overall sensorial experience. Ensuring the stability of dentifrices to ensure deliverance of the desired flavor profile is an important aspect in dentifrice formulation.

Accordingly, there remains a need for novel calcium abrasive, e.g., calcium carbonate, based dentifrices.

BRIEF SUMMARY

Provided is an oral care composition, e.g., a dentifrice, comprising a calcium abrasive, e.g., calcium carbonate, potassium nitrate ($KNO_3$), and a basic amino acid, in free or salt form, e.g., arginine, in free or salt form, e.g., arginine bicarbonate, wherein the potassium nitrate is present in an amount of 0.1-1% by weight of the composition, e.g., less than 1% by weight of the composition, e.g., 0.2-1% by weight of the composition, e.g., 0.2-0.8% by weight of the composition, e.g., 0.2-0.6% by weight of the composition, e.g., 0.2-0.5% by weight of the composition, e.g., 0.3-1% by weight of the composition, e.g., 0.3-0.8% by weight of the composition, e.g., 0.3-0.6% by weight of the composition, e.g., 0.3-0.5% by weight of the composition, e.g., 0.1% by weight of the composition, e.g., 0.2% by weight of the composition, e.g., 0.3% by weight of the composition, e.g., 0.4% by weight of the composition, e.g., 0.5% by weight of the composition.

Further provided are methods of using the oral care compositions disclosed herein.

Further areas of applicability of the present disclosure will become apparent from the detailed description provided hereinafter. It should be understood that the detailed description and specific examples, while indicating preferred embodiments, are intended for purposes of illustration only and are not intended to limit the scope of the disclosure.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The inventors have found that inclusion of potassium nitrate, which has high affinity to water and a high water holding capacity, incorporated at 0.1-1% by weight of the composition, in dentifrices comprising a calcium abrasive, e.g., calcium carbonate, and a basic amino acid, in free or salt form, e.g., arginine bicarbonate, may address the stability issues of such dentifrices. For instance, as shown in the example, dentifrices comprising calcium carbonate, arginine bicarbonate, and potassium nitrate did not show syneresis, color fading, and/or color migration even upon exposure to high temperature and high humidity.

Ensuring the stability of dentifrices comprising a calcium abrasive, e.g., calcium carbonate, and a basic amino acid, e.g., arginine bicarbonate, ensures that such dentifrices can deliver the desired flavor profile and aesthetics.

Provided is an oral care composition (Composition 1), e.g., a dentifrice, comprising a calcium abrasive, e.g., calcium carbonate, potassium nitrate ($KNO_3$), and a basic amino acid, in free or salt form, e.g., arginine, in free or salt form, e.g., arginine bicarbonate, wherein the potassium nitrate is present in an amount of 0.1-1% by weight of the composition, e.g., less than 1% by weight of the composition, e.g., 0.2-1% by weight of the composition, e.g., 0.2-0.8% by weight of the composition, e.g., 0.2-0.6% by weight of the composition, e.g., 0.2-0.5% by weight of the composition, e.g., 0.3-1% by weight of the composition, e.g., 0.3-0.8% by weight of the composition, e.g., 0.3-0.6% by weight of the composition, e.g., 0.3-0.5% by weight of the composition, e.g., 0.1% by weight of the composition, e.g., 0.2% by weight of the composition, e.g., 0.3% by weight of the composition, e.g., 0.4% by weight of the composition, e.g., 0.5% by weight of the composition.

In further embodiments, provided is:

1.1 Composition 1, wherein the calcium abrasive, e.g., calcium carbonate, is present in an amount of 30-60% by weight of the composition, e.g., 40-60% by weight of the composition, e.g., 40-50% by weight of the composition, e.g., 43% by weight of the composition.

1.2 Composition 1 or 1.1, wherein the calcium abrasive is dicalcium phosphate.

1.3 Composition 1 or 1.1, wherein the calcium abrasive is calcium carbonate.

1.4 Composition 1.3, wherein the calcium carbonate comprises natural calcium carbonate.

1.5 Composition 1.4, wherein the natural calcium carbonate is present in an amount of 10-50% by weight of the composition, e.g., 10-30% by weight of the composition, e.g., 20-50% by weight of the composition, e.g., 20% by weight of the composition, e.g., 42% by weight of the composition.

1.6 Composition 1.4 or 1.5, wherein the natural calcium carbonate is refined natural calcium carbonate.

1.7 Any of compositions 1.3-1.6, wherein the calcium carbonate comprises precipitated calcium carbonate.

1.8 Composition 1.7, wherein the precipitated calcium carbonate is present in an amount of 10-50% by weight of the composition, e.g., 10-30% by weight of the composition, e.g., 20-50% by weight of the composition, e.g., 24% by weight of the composition, e.g., 43-44% by weight of the composition, e.g., 43% by weight of the composition, e.g., 44% by weight of the composition.

1.9 Any of compositions 1.3-1.8, wherein the calcium carbonate comprises natural calcium carbonate and precipitated calcium carbonate.

1.10 Composition 1.9, wherein the natural calcium carbonate is present in an amount of 10-50% by weight of the composition, e.g., 10-30% by weight of the composition, e.g., 20% by weight of the composition, and the precipitated calcium carbonate is present in an amount of 10-50% by weight of the composition, e.g., 10-30% by weight of the composition, e.g., 24% by weight of the composition.

1.11 Composition 1.9 or 1.10, wherein the natural calcium carbonate is refined natural calcium carbonate.

1.12 Any of the preceding compositions, wherein the basic amino acid, in free or salt form, e.g., arginine, in free or salt form, e.g., arginine bicarbonate, is present in an amount of 0.1-20% by weight of the composition, e.g., 1-10% by weight of the composition, e.g., 1-5% by weight of the composition, e.g., 1-3% by weight of the composition, e.g., 1-2% by weight of the composition.

1.13 Any of the preceding compositions, wherein the basic amino acid, in free or salt form, is arginine, in free or salt form.

1.14 Composition 1.13, wherein the arginine, in free or salt form, is L-arginine, in free or salt form.

1.15 Composition 1.13 or 1.14, wherein the arginine, in free or salt form, is selected from one or more of arginine hydrochloride, arginine phosphate, arginine sulfate, and arginine bicarbonate, e.g., arginine bicarbonate.

1.16 Any of the preceding compositions, wherein the composition comprises one or more humectants.

1.17 Composition 1.16, wherein the one or more humectants, e.g., sorbitol, are present in an amount of equal to or less than 50% by weight of the composition, e.g., equal to or less than 40% by weight of the composition, e.g., equal to or less than 30% by weight of the composition, e.g., in an amount of 20-40% by weight of the composition, e.g, in an amount of 20-30% by weight of the composition.

1.18 Composition 1.16 or 1.17, wherein the one or more humectants is sorbitol.

1.19 Composition 1.18, wherein the sorbitol is present in an amount of equal to or less than 50% by weight of the composition, e.g., equal to or less than 40% by weight of the composition, e.g., equal to or less than 30% by weight of the composition, e.g., in an amount of 20-40% by weight of the composition, e.g., in an amount of 20-30% by weight of the composition.

1.20 Any of the preceding compositions, wherein the composition comprises one or more fluoride sources.

1.21 Composition 1.20, wherein the one or more fluoride sources are selected from stannous fluoride, sodium fluoride, potassium fluoride, sodium monofluorophosphate, sodium fluorosilicate, ammonium fluorosilicate, amine fluoride, and ammonium fluoride.

1.22 Composition 1.20 or 1.21, wherein the one or more fluoride sources is sodium monofluorophosphate.

1.23 Any of compositions 1.20-1.22, wherein the one or more fluoride sources, e.g., sodium monofluorophosphate, are present in an amount of 0.1-2% by weight of the composition, e.g., 0.1-1% by weight of the composition.

1.24 Any of the preceding compositions, wherein the composition comprises water.

1.25 Any of the preceding compositions, wherein the composition comprises one or more of an alkali metal silicate, a thickener, a flavorant, a colorant, an alkali metal bicarbonate, a surfactant, and a preservative, e.g., wherein the composition comprises one or more of sodium silicate, carrageenan, thickening silica, sodium saccharin, titanium dioxide, sodium bicarbonate, sodium lauryl sulfate, and benzyl alcohol.

1.26 Any of the preceding compositions, wherein the composition comprises one or more of:

(i) an alkali metal silicate, e.g., sodium silicate, in an amount of equal to or less than 2% by weight of the composition, e.g., equal to or less than 1% by weight of the composition, e.g., equal to or less than 0.5% by weight of the composition;

(ii) a thickener, e.g., carrageenan and/or thickening silica, in an amount of equal to or less than 2% by weight of the composition, e.g., equal to or less than 1.5% by weight of the composition, e.g., 1.1% by weight of the composition;

(iii) a flavorant, e.g., sodium saccharin, in an amount of equal to or less than 2% by weight of the composition, e.g., 0.1-2% by weight of the composition;

(iv) a colorant, e.g., titanium dioxide, in an amount of equal to or less than 2% by weight of the composition;

(v) an alkali metal carbonate, e.g., sodium bicarbonate, in an amount of equal to or less than 2% by weight of the composition, e.g., less than 1% by weight of the composition, e.g., 0.5% by weight of the composition;

(vi) a surfactant, e.g., sodium lauryl sulfate, in an amount of equal to or less than 3% by weight of the composition, e.g., 2-3% by weight of the composition, e.g., 2.3% by weight of the composition; and (vii) a preservative, e.g., benzyl alcohol, in an amount of equal to or less than 1% by weight of the composition.

1.27 Any of the preceding compositions, wherein the composition comprises water in an amount of 10-70% by weight of the composition, e.g., 10-60% by weight of the composition, e.g., 10-40% by weight of the composition, e.g., 20-40% by weight of the composition, e.g., 20-30% by weight of the composition. This amount of water includes the water which is added plus that amount which is introduced with other materials such as with sorbitol or any other components of the composition.

1.28 Any of the preceding compositions, wherein the potassium nitrate is present in an amount effective to enhance the stability, e.g., physical and/or cosmetic stability, of the composition, e.g., wherein the potassium nitrate is present in an amount effective to prevent one or more of syneresis, tip/neck/wall separation, color fading, and color migration.

1.29 Any of the preceding compositions, wherein the composition is a dentifrice, e.g., a toothpaste, e.g., a paste or a gel.

In some embodiments, the oral care compositions disclosed herein, e.g., Composition 1, e.g., any of compositions 1.1-1.29, comprise calcium carbonate. In some embodiments, the calcium carbonate comprises natural calcium carbonate. Natural calcium carbonate may be found in rocks such as chalk, limestone, marble, and travertine and is the principle component of egg shells and the shells of mollusks. In some embodiments, the natural calcium carbonate is a finely ground limestone which may optionally be refined or partially refined to remove impurities. In some embodiments, ≤0.3% of the refined natural calcium carbonate is retained on 325 Mesh. In some embodiments, the calcium carbonate comprises precipitated calcium carbonate. In some embodiments, the precipitated calcium carbonate is made by calcining limestone to make calcium oxide (lime), which is then converted back to calcium carbonate by reaction with carbon dioxide in water. In some embodiments, the precipitated calcium carbonate is more friable and more porous, thus having lower abrasivity and higher water absorption, than natural calcium carbonate. In some embodiments, ≤0.1% of the precipitated calcium carbonate is retained on 150 micron mesh. In some embodiments, ≤0.5% of the precipitated calcium carbonate is retained on 75 micron mesh.

In some embodiments, the oral care compositions disclosed herein, e.g., Composition 1, e.g., any of compositions 1.1-1.29, comprise one or more humectants. Any suitable humectant may be employed including, without limitation, polyhydric alcohols (polyols) such as propylene glycol, glycerin, sorbitol, xylitol, low molecular weight polyethylene glycols (PEGs), and a combination of two or more thereof. Humectants may, for example, prevent hardening of paste or gel compositions upon exposure to air. Certain humectants may also impart desirable sweetness of flavor to the compositions. In some embodiments, the one or more humectants are present in the oral care compositions disclosed herein, e.g., Composition 1, e.g., any of compositions 1.1-1.29, in an amount of equal to or less than 50% by weight of the composition, e.g., in an amount of 20-40% by weight of the composition. In some embodiments, the humectant is sorbitol.

In some embodiments, the oral care compositions disclosed herein, e.g., Composition 1, e.g., any of compositions 1.1-1.29, comprise one or more fluoride sources—i.e., a fluoride-containing compound having a beneficial effect on the care and hygiene of the oral cavity, for example, diminution of enamel solubility in acid and protection of the teeth against decay. Any suitable fluoride source may be employed including, without limitation, sodium fluoride, stannous fluoride, potassium fluoride, potassium stannous fluoride, potassium fluorozirconate, sodium hexafluorostannate, stannous chlorofluoride, sodium monofluorophosphate (MFP), and a combination of two or more thereof. Where present, the fluoride source may provide fluoride ion in amounts sufficient to supply 25-25,000 ppm of fluoride ions, generally at least 500 ppm, e.g., 500-2000 ppm, e.g., 1000-1600 ppm, e.g., 1450 ppm. The appropriate level of fluoride will depend on the particular application. A toothpaste for general consumer use would typically have 1000-1500 ppm, e.g., 1100 ppm, e.g., 1000 ppm, with pediatric toothpaste having somewhat less. A dentifrice or coating for professional application could have as much as 5,000 or even 25,000 ppm fluoride. The amount by weight of these materials, which dissociate or release fluoride or fluorine-containing ions, will depend on the molecular weight of the counterion as well as on the particular application, but suitably may be present in an effective but non-toxic amount, usually within the range of 0.1-2% by weight of the composition. In some embodiments, the fluoride source is selected from sodium fluoride, stannous fluoride, sodium monofluorophosphate, and a combination of two or more thereof. In some embodiments, the fluoride source is sodium monofluorophosphate in an amount of 0.5-1% by weight of the composition, e.g., 0.6-0.9% by weight of the composition, e.g., 0.7-0.8% by weight of the composition, e.g., 0.76% (about 1000 ppm fluoride ion) by weight of the composition.

In some embodiments, the oral care compositions disclosed herein, e.g., Composition 1, e.g., any of compositions 1.1-1.29, comprise water. Water employed in the preparation of commercial oral care compositions should be deionized and free of organic impurities. In some embodiments, water makes up the balance of the oral care compositions. In some embodiments, the oral care compositions disclosed herein, e.g., Composition 1, e.g., any of compositions 1.1-1.29, comprise water in an amount of 10-70% by weight of the composition, e.g., 10-60% by weight of the composition, e.g., 10-40% by weight of the composition, e.g., 20-40% by weight of the composition, e.g., 20-30% by weight of the composition. This amount of water includes the water which is added plus that amount which is introduced with other materials such as with sorbitol or any other components of the composition. In some embodiments, the amount of water which is added is 10-30% by weight of the composition, e.g., 10-20% by weight of the composition.

In some embodiments, the oral care compositions disclosed herein, e.g., Composition 1, e.g., any of compositions 1.1-1.29, comprise an alkali metal silicate. In some embodiments, the alkali metal is sodium, e.g., sodium silicate. Sodium silicate is available as a 10-40% aqueous solution. In some embodiments, the sodium silicate is neutral sodium silicate. In some embodiments, the sodium silicate is alkaline sodium silicate. In some embodiments, an aqueous solution of the alkali metal silicate, e.g., a 36.67% aqueous solution of sodium silicate, e.g., N-Silicate (1:3.26-41BE), is added to the composition in an amount of 0.1-2% by weight of the composition, e.g., 1% by weight of the composition.

In some embodiments, the oral care compositions disclosed herein, e.g., Composition 1, e.g., any of compositions 1.1-1.29, comprise one or more thickeners or binders, which may impart a desired consistency and/or mouth feel to the composition. Any suitable thickener or binder may be employed including, without limitation, carbomers (also known as carboxyvinyl polymers), carrageenans (also known as Irish moss and more particularly 1-carrageenan (iota-carrageenan)), cellulosic polymers such as hydroxyethylcellulose, carboxymethylcellulose (CMC) and salts thereof, e.g., sodium CMC, natural gums such as gum karaya, xanthan gum, gum arabic, and gum tragacanth, inorganic thickeners such as colloidal magnesium aluminum silicate, colloidal silica, thickening silica, and the like, and a combination of two or more thereof. In some embodiments, the one or more thickeners are selected from carrageenan, thickening silica, and a combination thereof. In some embodiments, the oral care compositions disclosed herein, e.g., Composition 1, e.g., any of compositions 1.1-1.29, comprise carrageenan. In some embodiments, the oral care compositions disclosed herein, e.g., Composition 1, e.g., any of compositions 1.1-1.29, comprise thickening silica. In some embodiments, the oral care compositions disclosed herein, e.g., Composition 1, e.g., any of compositions 1.1-1.29, comprise carrageenan and thickening silica. In some embodiments, the one or more thickeners or binders, e.g., carrageenan and/or thickening silica, are present in the oral care compositions disclosed herein, e.g., Composition 1, e.g., any of compositions 1.1-1.29, in an amount of 0.01-15% by weight of the composition, e.g., 0.1-10% by weight of the composition, e.g., 0.1-5% by weight of the composition, e.g., 0.1-2% by weight of the composition, e.g., 1-2% by weight of the composition. In some embodiments, carrageenan is present in the oral care compositions disclosed herein, e.g., Composition 1, e.g., any of compositions 1.1-1.29, in an amount of 0.01-15% by weight of the composition, e.g., 0.1-10% by weight of the composition, e.g., 0.1-5% by weight of the composition, e.g., 0.1-2% by weight of the composition. In some embodiments, thickening silica, is present in the oral care compositions disclosed herein, e.g., Composition 1, e.g., any of compositions 1.1-1.29, in an amount of 0.01-15% by weight of the composition, e.g., 0.1-10% by weight of the composition, e.g., 0.1-5% by weight of the composition, e.g., 0.1-2% by weight of the composition. In some embodiments, carrageenan is present in the oral care compositions disclosed herein, e.g., Composition 1, e.g., any of compositions 1.1-1.29, in an amount of 0.01-15% by weight of the composition, e.g., 0.1-10% by weight of the composition, e.g., 0.1-5% by weight of the composition, e.g., 0.1-2% by weight of the composition, and thickening silica, is present in an amount of 0.01-15% by weight of the composition, e.g., 0.1-10% by weight of the composition, e.g., 0.1-5% by weight of the composition, e.g., 0.1-2% by weight of the composition.

In some embodiments, the oral care compositions disclosed herein, e.g., Composition 1, e.g., any of compositions 1.1-1.29, comprise one or more flavorants. Any suitable flavorant, e.g., sweetening agent, may be employed including, without limitation, flavoring oils (e.g., oil of spearmint, peppermint, wintergreen, clove, sage, eucalyptus, marjoram, cinnamon, lemon, and orange), sucrose, sucralose, lactose, maltose, xylitol, stevia, sodium cyclamate, perillartine, aspartame, liquorice, saccharin or a salt thereof, and a combination of two or more thereof. In some embodiments, the flavorant is sodium saccharin. In some embodiments, the oral care compositions disclosed herein, e.g., Composition 1, e.g., any of compositions 1.1-1.29, comprise the one or more flavorants, e.g., sodium saccharin, in an amount of 0.1-5% by weight of the composition, e.g., 0.1-2% by weight of the composition.

In some embodiments, the oral care compositions disclosed herein, e.g., Composition 1, e.g., any of compositions 1.1-1.29, comprise one or more colorants. Any suitable colorant may be employed including, without limitation, zinc oxide, talc, titanium dioxide, pigments, dyes, and a combination of two or more thereof. In some embodiments, the colorant is titanium dioxide. In some embodiments, the oral care compositions disclosed herein, e.g., Composition 1, e.g., any of compositions 1.1-1.29, comprise the one or more colorants, e.g., titanium dioxide, in an amount of 0.001-20% by weight of the composition, e.g., 0.1-10% by weight of the composition, e.g., 0.1-5% by weight of the composition.

In some embodiments, the oral care compositions disclosed herein, e.g., Composition 1, e.g., any of compositions 1.1-1.29, comprise one or more alkali metal bicarbonates, e.g., sodium bicarbonate, which may control the pH of the composition. The alkali metal bicarbonate, e.g., sodium bicarbonate, may also provide a synergistic effect with the potassium nitrate in arresting syneresis. In some embodiments, the oral care compositions disclosed herein, e.g., Composition 1, e.g., any of compositions 1.1-1.29, comprise the one or more alkali metal bicarbonates, e.g., sodium bicarbonate, in an amount of 0.1-1% by weight of the composition, e.g., 0.5% by weight of the composition.

In some embodiments, the oral care compositions disclosed herein, e.g., Composition 1, e.g., any of compositions 1.1-1.29, comprise one or more detergents or surfactants. Any suitable surfactant may be employed including, without limitation, anionic, nonionic, and amphoteric surfactants and combinations thereof. Surfactants may, for example, provide enhanced stability of the formulation, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonated monoglycerides of $C_{8-20}$ fatty acids, sarcosinates, taurates, and a combination of two or more thereof; for example sodium lauryl sulfate, sodium coconut monoglyceride sulfonate, sodium lauroyl sarcosinate, sodium lauroyl isoethionate, sodium laureth carboxylate, sodium dodecyl benzenesulfonate, and a combination of two or more thereof. In some embodiments, the surfactant is sodium lauryl sulfate. In some embodiments, the oral care compositions disclosed herein, e.g., Composition 1, e.g., any of compositions 1.1-1.29, comprise the one or more detergents or surfactants, e.g., sodium lauryl sulfate, in an amount of 0.01-10% by weight of the composition, e.g., 0.05-5% by weight of the composition, e.g., 1-5% by weight of the composition, e.g., 2-3% by weight of the composition.

In some embodiments, the oral care compositions disclosed herein, e.g., Composition 1, e.g., any of compositions 1.1-1.29, comprise one or more preservatives. Any suitable preservative may be employed including, without limitation, sodium benzoate, methyl paraben, propyl paraben, benzyl alcohol, ethanol, citric acid, potassium sorbate, salicylic acid, sorbic acid, inorganic sulfites, triclosan, flavors, and a combination of two or more thereof. In some embodiments, the preservative is benzyl alcohol. In some embodiments, the oral care compositions disclosed herein, e.g., Composition 1, e.g., any of compositions 1.1-1.29, comprise the one or more preservatives, e.g., benzyl alcohol, in an amount of 0.0001-1% by weight of the composition, e.g., 0.01-1% by weight of the composition.

As will be evident to one of skill in the art, some components of the compositions disclosed herein may perform multiple functions, and the identification of a compound as having one function herein is not meant to exclude its use for other functions in a particular composition. For example, a compound such as xylitol may function in the compositions disclosed herein as a sweetener, but also act as a humectant.

The oral care compositions disclosed herein, e.g., Composition 1, e.g., any of compositions 1.1-1.29, are intended for topical use in the mouth so salts for use in the oral care compositions disclosed herein should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Further provided is a method (Method 1) to:
(i) reduce or inhibit formation of dental caries,
(ii) reduce, repair, or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) increase relative levels of arginolytic bacteria,
(ix) reduce or inhibit microbial biofilm formation in the oral cavity,
(x) raise and/or maintain plaque pH at levels of at least pH about 5.5 following sugar challenge,
(xi) reduce or inhibit plaque formation in the oral cavity,
(xii) reduce erosion,
(xiii) whiten teeth,
(xiv) promote systemic health,
(xv) immunize or protect teeth against cariogenic bacteria, and/or
(xvi) clean teeth and oral cavity, comprising applying an effective amount of an oral care composition disclosed herein, e.g., Composition 1, e.g., any of compositions 1.1-1.29, to the oral cavity of a subject in need thereof.

Further provided is a method (Method 2) to improve oral health comprising applying an effective amount of an oral care composition disclosed herein, e.g., Composition 1, e.g., any of compositions 1.1-1.29, to the oral cavity of a subject in need thereof.

Further provided is the use (Use 1) of an oral care composition disclosed herein, e.g., Composition 1, e.g., any of compositions 1.1-1.29, to
(i) reduce or inhibit formation of dental caries,
(ii) reduce, repair, or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) increase relative levels of arginolytic bacteria,
(ix) reduce or inhibit microbial biofilm formation in the oral cavity,
(x) raise and/or maintain plaque pH at levels of at least pH about 5.5 following sugar challenge,
(xi) reduce or inhibit plaque formation in the oral cavity,
(xii) reduce erosion,
(xiii) whiten teeth,
(xiv) promote systemic health,
(xv) immunize or protect teeth against cariogenic bacteria, and/or
(xvi) clean teeth and oral cavity.

The methods disclosed herein, e.g., Methods 1 and 2, involve applying to the oral cavity a safe and effective amount of the oral care compositions disclosed herein, e.g., Composition 1, e.g., any of compositions 1.1-1.29. The oral care compositions and methods disclosed herein, e.g., Composition 1, e.g., any of compositions 1.1-1.29, e.g., Methods 1 and 2, are useful, inter alia, to cleanse and/or lubricate the oral cavity of a mammal, for example a human, and in particular to clean and/or lubricate the oral cavity and provide improved methods of promoting oral health and/or systemic health, including cardiovascular health, e.g., by reducing bacterial levels in the oral cavity.

Further provided is a method (Method 3) of preventing one or more of syneresis, color migration, and color degradation in an oral care composition, e.g., a dentifrice, comprising a calcium abrasive, e.g., calcium carbonate, and a basic amino acid, in free or salt form, e.g., arginine, in free or salt form, e.g., arginine bicarbonate, comprising adding an effective amount of potassium nitrate ($KNO_3$) to the oral care composition.

In further embodiments, provided is:

3.1 Method 3, wherein the potassium nitrate is added in an amount of 0.1-1% by weight of the composition, e.g., less than 1% by weight of the composition, e.g., 0.2-1% by weight of the composition, e.g., 0.2-0.8% by weight of the composition, e.g., 0.2-0.6% by weight of the composition, e.g., 0.2-0.5% by weight of the composition, e.g., 0.3-1% by weight of the composition, e.g., 0.3-0.8% by weight of the composition, e.g., 0.3-0.6% by weight of the composition, e.g., 0.3-0.5% by weight of the composition, e.g., 0.1% by weight of the composition, e.g., 0.2% by weight of the composition, e.g., 0.3% by weight of the composition, e.g., 0.4% by weight of the composition, e.g., 0.5% by weight of the composition.

3.2 Method 3 or 3.1, wherein the calcium abrasive, e.g., calcium carbonate, is present in an amount of 30-60% by weight of the composition, e.g., 40-60% by weight of the composition, e.g., 40-50% by weight of the composition, e.g., 43% by weight of the composition.

3.3 Any of the preceding methods, wherein the calcium abrasive is dicalcium phosphate.

3.4 Any of methods 3, 3.1, or 3.2, wherein the calcium abrasive is calcium carbonate.

3.5 Method 3.4, wherein the calcium carbonate comprises natural calcium carbonate.

3.6 Method 3.5, wherein the natural calcium carbonate is present in an amount of 10-50% by weight of the composition, e.g., 10-30% by weight of the composition, e.g., 20-50% by weight of the composition, e.g., 20% by weight of the composition, e.g., 42% by weight of the composition.

3.7 Method 3.5 or 3.6, wherein the natural calcium carbonate is refined natural calcium carbonate.

3.8 Any of methods 3.4-3.7, wherein the calcium carbonate comprises precipitated calcium carbonate.

3.9 Method 3.8, wherein the precipitated calcium carbonate is present in an amount of 10-50% by weight of the composition, e.g., 10-30% by weight of the composition, e.g., 20-50% by weight of the composition, e.g., 24% by weight of the composition, e.g., 43-44% by weight of the composition, e.g., 43% by weight of the composition, e.g., 44% by weight of the composition.

3.10 Any of methods 3.4-3.9, wherein the calcium carbonate comprises natural calcium carbonate and precipitated calcium carbonate.

3.11 Method 3.10, wherein the natural calcium carbonate is present in an amount of 10-50% by weight of the composition, e.g., 10-30% by weight of the composition, e.g., 20% by weight of the composition, and the precipitated calcium carbonate is present in an amount of 10-50% by weight of the composition, e.g., 10-30% by weight of the composition, e.g., 24% by weight of the composition.

3.12 Method 3.10 or 3.11, wherein the natural calcium carbonate is refined natural calcium carbonate.

3.13 Any of the preceding methods, wherein the basic amino acid, in free or salt form, e.g., arginine, in free or salt form, e.g., arginine bicarbonate, is present in an amount of 0.1-20% by weight of the composition, e.g., 1-10% by weight of the composition, e.g., 1-5% by weight of the composition, e.g., 1-3% by weight of the composition, e.g., 1-2% by weight of the composition.

3.14 Any of the preceding methods, wherein the basic amino acid, in free or salt form, is arginine, in free or salt form.

3.15 Method 3.14, wherein the arginine, in free or salt form, is L-arginine, in free or salt form.

3.16 Method 3.14 or 3.15, wherein the arginine, in free or salt form, is selected from one or more of arginine hydrochloride, arginine phosphate, arginine sulfate, and arginine bicarbonate, e.g., arginine bicarbonate.

3.17 Any of the preceding methods, wherein the composition comprises one or more humectants.

3.18 Method 3.17, wherein the one or more humectants, e.g., sorbitol, are present in an amount of equal to or less than 50% by weight of the composition, e.g., equal to or less than 40% by weight of the composition, e.g., equal to or less than 30% by weight of the composition, e.g., in an amount of 20-40% by weight of the composition, e.g, in an amount of 20-30% by weight of the composition.

3.19 Method 3.17 or 3.18, wherein the one or more humectants is sorbitol.

3.20 Method 3.19, wherein the sorbitol is present in an amount of equal to or less than 50% by weight of the composition, e.g., equal to or less than 40% by weight of the composition, e.g., equal to or less than 30% by weight of the composition, e.g., in an amount of 20-40% by weight of the composition, e.g., in an amount of 20-30% by weight of the composition.

3.21 Any of the preceding methods, wherein the composition comprises one or more fluoride sources.

3.22 Method 3.21, wherein the one or more fluoride sources are selected from stannous fluoride, sodium fluoride, potassium fluoride, sodium monofluorophosphate, sodium fluorosilicate, ammonium fluorosilicate, amine fluoride, and ammonium fluoride.

3.23 Method 3.21 or 3.21, wherein the one or more fluoride sources is sodium monofluorophosphate.

3.24 Any of methods 3.21-3.23, wherein the one or more fluoride sources, e.g., sodium monofluorophosphate, are present in an amount of 0.1-2% by weight of the composition, e.g., 0.1-1% by weight of the composition.

3.25 Any of the preceding methods, wherein the composition comprises water.

3.26 Any of the preceding methods, wherein the composition comprises one or more of an alkali metal silicate, a thickener, a flavorant, a colorant, an alkali metal bicarbonate, a surfactant, and a preservative, e.g., wherein the composition comprises one or more of sodium silicate, carrageenan, thickening silica, sodium saccharin, titanium dioxide, sodium bicarbonate, sodium lauryl sulfate, and benzyl alcohol.

3.27 Any of the preceding methods, wherein the composition comprises one or more of:

(i) an alkali metal silicate, e.g., sodium silicate, in an amount of equal to or less than 2% by weight of the composition, e.g., equal to or less than 1% by weight of the composition, e.g., equal to or less than 0.5% by weight of the composition;

(ii) a thickener, e.g., carrageenan and/or thickening silica, in an amount of equal to or less than 2% by weight of the composition, e.g., equal to or less than 1.5% by weight of the composition, e.g., 1.1% by weight of the composition;

(iii) a flavorant, e.g., sodium saccharin, in an amount of equal to or less than 2% by weight of the composition, e.g., 0.1-2% by weight of the composition;

(iv) a colorant, e.g., titanium dioxide, in an amount of equal to or less than 2% by weight of the composition;

(v) an alkali metal carbonate, e.g., sodium bicarbonate, in an amount of equal to or less than 2% by weight of the composition, e.g., less than 1% by weight of the composition, e.g., 0.5% by weight of the composition;

(vi) a surfactant, e.g., sodium lauryl sulfate, in an amount of equal to or less than 3% by weight of the composition, e.g., 2-3% by weight of the composition, e.g., 2.3% by weight of the composition; and (vii) a preservative, e.g., benzyl alcohol, in an amount of equal to or less than 1% by weight of the composition.

3.28 Any of the preceding methods, wherein the composition comprises water in an amount of 10-70% by weight of the composition, e.g., 10-60% by weight of the composition, e.g., 10-40% by weight of the composition, e.g., 20-40% by weight of the composition, e.g., 20-30% by weight of the composition. This amount of water includes the water which is added plus that amount which is introduced with other materials such as with sorbitol or any other components of the composition.

3.29 Any of the preceding methods, wherein the composition is a dentifrice, e.g., a toothpaste, e.g., a paste or a gel.

Enhancing oral health also provides benefits in systemic health, as the oral tissues can be gateways for systemic infections. Good oral health is associated with systemic health, including cardiovascular health. The compositions and methods disclosed herein are thus useful to enhance systemic health, including cardiovascular health.

EXAMPLE

Example 1

Control A and Compositions 1-4, according to the invention, are made as shown in Table 1. Samples of the respective compositions in tubes are maintained both at room temperature and under accelerated conditions (40° C./75% relative humidity) for 3 months. The compositions are analyzed by cutting open the tubes.

TABLE 1

| Ingredients | Control A | Composition 1 | Composition 2 | Composition 3 | Composition 4 |
|---|---|---|---|---|---|
| Sorbitol 70% | 30 | 30 | 30 | 30 | 30 |
| Thickeners | 1.1 | 1.1 | 1.1 | 1.1 | 1.1 |
| Sodium Monofluoro-phosphate | 0.76 | 0.76 | 0.76 | 0.76 | 0.76 |
| Sodium Bicarbonate | 0.5 | 0.5 | 0.5 | 0.5 | 0.5 |
| Water and minors | 18.4 | 18.3 | 18.2 | 18.1 | 17.9 |
| Liquid Sodium Silicate | 1 | 1 | 1 | 1 | 1 |
| Calcium Carbonate | 43 | 43 | 43 | 43 | 43 |
| Arginine Bicarbonate Solution | 2.7 | 2.7 | 2.7 | 2.7 | 2.7 |
| Potassium Nitrate ($KNO_3$) | — | 0.1 | 0.2 | 0.3 | 0.5 |
| Sodium Lauryl Sulphate | 2.3 | 2.3 | 2.3 | 2.3 | 2.3 |
| Preservatives | 0.3 | 0.3 | 0.3 | 0.3 | 0.3 |
| RT - 3 Months | Tip Syneresis | Tip Syneresis | Stable | Stable | Stable |
| 40° C./75% RH - 3 Months | Tip Syneresis | Tip Syneresis | Tip Syneresis | Stable | Stable |

The inclusion of $KNO_3$ arrests liquid separation from dentifrice at room temperature and at accelerated stability conditions compared to dentifrice without $KNO_3$. Higher levels of $KNO_3$ (0.3%, 0.5%) show less/no liquid separation compared to lower levels of $KNO_3$ (0.1%, 0.2%), signifying the role of $KNO_3$ in providing physical/cosmetic stability to the formulations.

What is claimed is:

1. An oral care composition comprising a calcium abrasive, potassium nitrate ($KNO_3$), and a basic amino acid, in free or salt form, wherein the potassium nitrate is present in an amount of 0.3-1% by weight of the composition, and wherein the composition is a dentifrice, wherein the calcium abrasive comprises calcium carbonate, wherein the basic amino acid, in free or salt form, comprises arginine, in free or salt form, wherein the calcium carbonate is present in an amount of 30-60% by weight of the composition, and wherein the arginine, in free or salt form, is present in an amount of 0.1-20% by weight of the composition.

2. The oral care composition of claim 1, wherein the potassium nitrate is present in an amount of 0.3-0.5% by weight of the composition.

3. The oral care composition of claim 1, wherein the calcium carbonate is present in an amount of 40-50% by weight of the composition.

4. The oral care composition of claim 1, wherein the calcium carbonate comprises natural calcium carbonate in an amount of 10-50% by weight of the composition and precipitated calcium carbonate in an amount of 10-50% by weight of the composition.

5. The oral care composition of claim 1, wherein the arginine, in free or salt form, is present in an amount of 1-10% by weight of the composition.

6. The oral care composition of claim 1, wherein the arginine, in free or salt form, is arginine bicarbonate.

7. The oral care composition of claim 1, wherein the composition further comprises one or more fluoride sources.

8. The oral care composition of claim 7, wherein the one or more fluoride sources are selected from stannous fluoride, sodium fluoride, potassium fluoride, sodium monofluorophosphate, sodium fluorosilicate, ammonium fluorosilicate, amine fluoride, and ammonium fluoride.

9. The oral care composition of claim 7, wherein the one or more fluoride sources are present in an amount of 0.1-2% by weight of the composition.

10. The oral care composition of claim 8, wherein the one or more fluoride sources is sodium monofluorophosphate.

11. The oral care composition of claim 1, wherein the composition further comprises one or more of an alkali metal silicate, a thickener, a flavorant, a colorant, an alkali metal bicarbonate, a surfactant, and a preservative.

12. The oral care composition of claim 11, wherein the composition comprises one or more of:

(i) an alkali metal silicate in an amount of equal to or less than 2% by weight of the composition;

(ii) a thickener in an amount of equal to or less than 2% by weight of the composition;

(iii) a flavorant in an amount of equal to or less than 2% by weight of the composition;

(iv) a colorant in an amount of equal to or less than 2% by weight of the composition;

(v) an alkali metal carbonate in an amount of equal to or less than 2% by weight of the composition;

(vi) a surfactant in an amount of equal to or less than 3% by weight of the composition; and (vii) a preservative in an amount of equal to or less than 1% by weight of the composition.

13. The oral care composition of claim 12, wherein the preservative is benzyl alcohol.

14. The oral care composition of claim 1, wherein the potassium nitrate is present in an amount effective to enhance the stability of the composition.

15. The oral care composition of claim 1, wherein the potassium nitrate is present in an amount effective to prevent one or more of syneresis, tip, neck or wall separation, color fading, and color migration.

16. The oral care composition of claim 1, wherein the composition is a toothpaste.

17. A method to:

(i) reduce or inhibit formation of dental caries, (ii) reduce, repair, or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) increase relative levels of arginolytic bacteria, (ix) reduce or inhibit microbial biofilm formation in the oral cavity, (x) raise and/or maintain plaque pH at levels of at least pH about 5.5 following sugar challenge, (xi) reduce or inhibit plaque formation in the oral cavity, (xii) reduce erosion, (xiii) whiten teeth, (xiv) promote systemic health, (xv) immunize or protect teeth against cariogenic bacteria, and/or (xvi) clean teeth and oral cavity, comprising applying an effective amount of an oral care composition of claim 1 to the oral cavity of a subject in need thereof.

18. A method of preventing one or more of syneresis, color migration, and color degradation in an oral care composition comprising a calcium abrasive and a basic amino acid, in free or salt form, comprising adding potassium nitrate ($KNO_3$) in an amount of 0.3-1% by weight of the composition to the oral care composition, wherein the compositions is a dentifrice, wherein the calcium abrasive comprises calcium carbonate, wherein the basic amino acid, in free or salt form, comprises arginine, in free or salt form, wherein the calcium carbonate is present in an amount of 30-60% by weight of the composition, and wherein the arginine, in free or salt form, is present in an amount of 0.1-20% by weight of the composition.

* * * * *

UNITED STATES PATENT AND TRADEMARK OFFICE

CERTIFICATE OF CORRECTION

PATENT NO. : 11,020,329 B2
APPLICATION NO. : 16/504642
DATED : June 1, 2021
INVENTOR(S) : Shashank Potnis et al.

It is certified that error appears in the above-identified patent and that said Letters Patent is hereby corrected as shown below:

In the Claims

In Column 15, Line 13, in Claim 18, delete “compositions” and insert -- composition --, therefor.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*